United States Patent [19]
Beard et al.

[11] 4,165,332
[45] Aug. 21, 1979

[54] PREPARATION OF ALIPHATIC PERCHLORATES AND OF TRIFLUOROMETHANE SULFONATES

[75] Inventors: Charles D. Beard, Yorktown Heights, N.Y.; Kurt Baum, Pasadena, Calif.

[73] Assignee: The United States of America as represented by the Secretary of the Navy, Washington, D.C.

[21] Appl. No.: 647,395

[22] Filed: Jan. 8, 1976

[51] Int. Cl.$^2$ .............................................. C07C 71/00
[52] U.S. Cl. ............................ 260/453 R; 260/456 F
[58] Field of Search ........................ 260/456 F, 453 R

[56] References Cited
U.S. PATENT DOCUMENTS
2,732,398  1/1956  Brice et al. ........................ 260/456 F

OTHER PUBLICATIONS

Beard et al, J. Org. Chem., vol. 39, No. 26, Dec. 27, 1974.
Burdon et al, Tetrahedron, vol. 21, pp. 1-4, Pergamon Press, Ltd., (1965).
Dafforn et al., Tetra. Letter, (36), 3159-3162, (1970).
Gramstad et al, J. Chem. Soc., 173 (1956).

*Primary Examiner*—James O. Thomas, Jr.
*Assistant Examiner*—G. T. Breitenstein
*Attorney, Agent, or Firm*—R. S. Sciascia; Philip Schneider; Thomas McDonnell

[57] ABSTRACT

The formation of predominantly primary aliphatic perchlorates and trifluoromethanesulfonates by reacting the corresponding silver salt with primary aliphatic halides in benzene at a temperature from about 5° C. to about 50° C. Primary aliphatic perchlorates and trifluoromethanesulfonates are excellent alkylating agents for amines, alcohols, and nitroalcohols.

10 Claims, No Drawings

PREPARATION OF ALIPHATIC PERCHLORATES AND OF TRIFLUOROMETHANE SULFONATES

BACKGROUND OF THE INVENTION

This invention pertains generally to organic synthesis and in particular to organic synthesis with isomeric exclusively.

Trifluoromethanesulfonates are often referred to as triflates. The term will also be used hereinafter for trifluoromethanesulfonate.

Alkyl perchlorates and triflates are excellent alkylating agents for weakly nucleophilic compounds such as amines, alcohols, and nitroalcohols. Numerous methods are known for the preparation of perchlorate compounds. Examplary of the known perchlorate synthesis are the reaction of as alkyl halide with silver perchlorate in carbon tetrachloride or heptane, the reaction of barium alkyl sulfate with barium perchlorate, the reaction of diazomethane with perchloric acid, and the reaction disclosed in U.S. Pat. No. 3,660,455. All of the cited reactions produced either an isomer other than the primary configuration or produced a mixture of isomers. The only known method of producing a primary alkyl perchlorate is disclosed in Baum and Beard. *Reactions of Dichlorine Heptoxide with Alcohols.* in J. Amer. Chem. Soc. 96:10. p. 3233-3237 (May 15, 1974). This method, however, has the disadvantages of being slightly difficult and expensive.

Much less is known concerning the preparation of alkyl triflates. The most versatile and practical method is disclosed in patent application Ser. No. 515,383, filed on Oct. 16, 1974, by Kurt Baum and Charles D. Beard. While the method, unlike the other known methods, is able to produce alkyl triflates greater than ethyl triflate, this method is also slightly difficult and expensive in that an anhydride is prepared.

SUMMARY OF THE INVENTION

It is, therefore, an object of the invention to provide a method of preparing predominantly primary aliphatic perchlorate and triflates.

Another object of the present invention is to prepare these perchlorates and triflates in a high yield, with a high purity, in safety, and with a low cost.

These and other objects are achieved by the virtual elimination of isomerization through the substitution reaction of an aliphatic halide with silver perchlorates or triflates in benzene.

DETAILED DESCRIPTION OF THE INVENTION

The reactions by which the present invention proceeds are diagramatically illustrated in the following example:

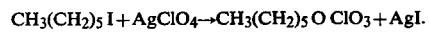

By the method of this invention any primary aliphatic perchlorate or triflate can be prepared without any appreciable isomerization. Alkyl perchlorates and triflates with 3 to 10 carbon atom would be preferred due to their greater usefulness. Of course any secondary or tertiary alkyl, along with unsaturated aliphatic perchlorates and triflates can be prepared by this method. However the importance of this invention lies in the preparation of primary aliphatic perchlorates or triflates having from 3 to 10 carbon atoms without any appreciable isomerization. The reactants can be mixed together in any order or in any manner. The aliphatic halide can be an iodide, bromide or chloride. The bromides and chlorides are not preferred on account of the increased reaction time resulting from their use. It is very probable that some reactions may not proceed at all. On the other hand, this substitution reaction occurs quickly for all aliphatic iodides.

The reaction time can be reduced further by an inclusion of an excess of the silver salt. An excess of 10-15 mole percent of the stoichiometric amount has been found to give the best results in terms of cost and reaction time. It should be noted that since the reaction is a single substitution reaction the reactants may be mixed in any amounts without affecting the product. Unlike other reactions of this type, the reactions of the present invention are only partially heterogenous. Hence the particle size of the silver salt has little effect on the reaction time.

The reaction solvent is benzene. As a safety precaution the amount of benzene should be such that the product solution is no more than a 20% solution. It is, of course, possible to have less benzene, but the chance for an explosion is greater. Anything is excess of a 75% product solution would be extremely dangerous.

The reaction mixture is agitated sufficiently, by any means, to insure a uniform distribution of the reactants. The reaction temperature is from about 5° to about 50° C., but preferrably from 20° C. to 30° C. The end point can be detected by monitoring the reaction by nmr.

The following comparative examples are given to demonstrate the advantages of the present invention. A summary of these examples is given in Tables I&II. It is to be understood that these examples are given by way of illustration and are not meant to limit the specification or the claims to follow in any manner.

TABLE I

Reactions of Aliphatic Iodides with Silver Perchlorate

| Starting Material | Product | Solvent | Yield (%) |
|---|---|---|---|
| $CH_3CH_2CH_2I$ | $CH_3CH_2CH_2OClO_3$ | $C_6H_6$ | 91 |
| $CH_3(CH_2)_3CH_2I$ | $CH_3(CH_2)_3CH_2OClO_3$ | $C_6H_6$ | 86 |
| $CH_3(CH_2)_4CH_2I$ | $CH_3(CH_2)_4CH_2OClO_3$ | $C_6H_6$ | 87 |

TABLE II

Reactions of Aliphatic Iodides with Silver Triflate

| Starting Material | Product | Solvent | Yield (%) |
|---|---|---|---|
| $CH_3CH_2CH_2I$ | $CH_3CH_2CH_2OSO_2CF_3$ | $C_6H_6$ | 92 |
| $CH_3(CH_2)_3CH_2I$ | $CH_3(CH_2)_3CH_2OSO_2CF_3$ | $C_6H_6$ | 82 |
| $CH_3(CH_2)_4CH_2I$ | $CH_3(CH_2)_4CH_2OSO_2CF_3$ | $C_6H_6$ | 91 |
| $CH_3(CH_2)_8CH_2I$ | $CH_3(CH_2)_8CH_2OSO_2CF_3$ | $C_6H_6$ | 93 |

In the examples, nmr spectra were recorded with a Varian T-60 spectrometer, and the ir spectra were recorded with a Perkin-Elmer 700 spectrometer. Anhydrous grade silver perchlorate was dried azeotropically before use. Silver triflate, prepared from triflic acid and silver oxide, was dried by azeotroping with benzene until the salt was soluble. At which time, the solvent was removed and the residue was dried for 5 hours at 80° (0.05 mm).

EXAMPLE I

Reactions of Silver Perchlorate with Propyl Iodide

Propyl iodide (0.170 g, 1 mmol) was added with stirring to 0.207 g (1 mmol) of anhydrous silver perchlorate and 3 ml of carbon tetrachloride at 0°. After 1 hr., nmr analysis of the solution, using chlorobenzene as a quantitative standard showed a quantitative yield of a mixture of propyl perchlorate (40%) and isopropyl perchlorate (60%). Variations of up to 10% were observed in yields of the components but the total remained quantitative. Identical results were obtained using pentane or 1,1,2-trichlorotrifluoroethane as the solvent. Methylene chloride gave a 92% yield of a mixture of propyl perchlorate (62%) and isopropyl perchlorate (38%). In an experiment identical to that above using carbon tetrachloride, but with twice the theoretical amount of propyl iodide, the product consisted of 41% isopropyl perchlorate and 59% propyl perchlorate. Four times the theoretical amount of propyl iodide gave 23% isopropyl perchlorate and 77% propyl perchlorate.

The use of benzene as the reaction solvent required 18 hours of stirring at room temperature for completion. The benzene solution was filtered, washed with water and dried over magnesium sulfate. Nmr analysis showed a 91% yield of propyl perchlorate and no trace of isopropyl perchlorate. The benzene solution was added to an equal volume of 10% lithium bromide in acetone and the mixture was washed with water and dried. Nmr and glpc showed propyl bromide but no isopropyl bromide. No rearrangement was observed when ten times the theoretical amount of silver perchlorate (2.07 g) was used, mainly out of solution.

The reaction of equivalent amounts of propyl iodide and silver perchlorate for 18 hours, as above, in a solvent consisting of 33% benzene and 67% carbon tetrachloride gave a 90% yield of perchlorates consisting of 50% propyl perchlorate and 50% isopropyl perchlorate. A solvent consisting of 67% benzene and 33% carbon tetrachloride gave a 91% yield consisting of 15% isopropyl perchlorate and 85% propyl perchlorate.

Propyl perchlorate and isopropyl perchlorate were unchanged in control experiments in the presence of silver perchlorate and silver iodide.

EXAMPLES II AND III

Preparation of Aliphatic Perchlorate Solutions

Equivalent amounts of silver perchlorate were reacted as above with pentyl iodide and hexyl iodide to give the corresponding perchlorates with no detectable isomeric products. The respective solvents and yields are shown in Table I.

EXAMPLE IV

Reaction of Hexyl Iodide with Silver Perchlorate in Carbon Tetrachloride

The above procedure was used. Nmr analysis showed that the product consisted of 42% 1-hexyl perchlorate could not be resolved by nmr. The solution was added to an equal volume of 10% lithium bromide in acetone and the mixture was washed with water. A mixture of 2-bromohexane and 3-bromohexane was isolated by preparative glpc. Nmr analysis, by comparison with authentic samples, showed a 4:1 ratio of 2-bromohexane to 3-bromohexane. In control experiments, 1-hexyl perchlorate gave a quantitative yield of 1-bromohexane, and the secondary perchlorates each gave a 50% yield of the corresponding bromide.

EXAMPLE V

Reaction of Silver Triflate with Propyl Iodide

Propyl iodide (0.170 g, 1 mmol) was added with stirring to 0.259 g (1 mmol) of silver triflate in 3 ml of carbon tetrachloride at ambient temperature. Yields were determined after 2 hours by both proton and fluorine nmr using benzotrifluoride as a quantitative standard. A 97% yield of triflates was obtained consisting of 34% propyl triflate and 66% isopropyl triflate. The yields of the components varied +10% by the total was always nearly quantitative. The same results were obtained using 1,1,2-trichlorotrifluoroethane or pentane as solvent. Methylene chloride gave a 95% yeild consisting of 59% propyl triflate and 41% isopropyl triflate. Using benzene as solvent (18 hours) gave a 92% yield of propyl triflate with no isopropyl triflate. A solvent consisting of 33% benzene and 67% 1,1,2-trichlorotrifluoroethane gave a 98% yield containing 43% propyl triflate and 57% isopropyl triflate; 50% benzene, 50% 1,1,2-trichlorotrifluoroethane gave a 98% yield with 51% propyl triflate, 49% isopropyl triflate; 67% benzend, 33% 1,1,2-trichlorotrifluoroethane gave a 94% yield with 77% propyl triflate, 23% isopropyl triflate.

Propyl Triflate

A solution of 0.30 g (5 mmol) of propanol and 0.395 g (2 mmol) of pyridine in 5 ml of carbon tetrachloride was added dropwise, with stirring to a solution of 1.41 g (5 mmol) of triflic anhydride in 10 ml of carbon tetrachloride at 0°. In 15 min the solution was filtered, washed with water, and dried over magnesium sulfate. Nmr analysis using chlorobenzene as a quantitative reference; showed an 86% yield of propyl triflate; proton nmr (CCl$_4$) $\delta$4.45 (t, 2H J=6 Hz, CH$_2$O—), 1.83 (m, 2H, CH$_2$CH$_2$O—) and 1.08 ppm (t, 3H, J=6 Hz, CH$_3$); fluorine nmr (CCl$_4$) $\phi$75.80 ppm (s); ir (CCl$_4$) 2990 (m), 1460 (w), 1420 (vs), 1250 (s), 1220 (vs), 1155 (vs) and 950 cm$^{-1}$ (vs).

EXAMPLE VI-VIII

Preparation of aliphatic Triflate Solutions

By the procedure used above for propyl iodide, equivalent amounts of silver triflate were reacted with pentyl iodide, hexyl iodide and decyl iodide to give the corresponding triflates. The respective solvents and yields are shown in Table 2.

Pentyl Triflate

Pentyl iodide (0.91 g, 4.6 mmol) was added dropwise with stirring to a partial suspension of 2.40 g (9.2 mmol) of silver triflate in 25 ml of benzene. The mixture was stirred 18 hours, filtered, washed with water, dried over magnesium sulfate and distilled to give 0.785 g (82%) of pentyl triflate, bp 55-57 (1.5 mm), with spectra identical with those reported.

Hexyl Triflate

Hexyl iodide (2.12 g, 10 mmol) was reacted with 2.57 g (10 mmol) of silver triflate in 50 ml of benzene as above to give 2.13 g (91%) of hexyl triflate, bp 26°-28° (0.1 mm); proton nmr (CCl$_4$) 4.43 (t, 2H, J=6 Hz, CH$_2$O), 1.80 (m, 2H, CH$_2$CH$_2$O), 1.26 (m, 6H, CH$_2$) and 0.90 ppm (m, 3H, CH$_3$); fluorine nmr (CCl$_4$) $\phi$75.8 ppm (S); ir (CCl$_4$) 1420, 1225, 1155, and 940 cm$^{-1}$ (SO$_3$CF$_3$).

Anal. Calcd for C$_7$H$_{13}$F$_3$SO$_3$: C, 35.90; h, 5.59. Found: C, 35.81; H, 5.72.

Decyl Triflate

Decyl iodide (4.02 g, 15 mmol) was reacted by the above procedure with 5.14 g (20 mmol) of silver triflate in 100 ml of benzene. The washed and dried benzene solution was filtered through silicic acid and stripped of solvent to give 4.05 g (93%) of decyl triflate, a colorless oil: proton nmr (CDCl$_3$) $\delta$4.42 (t, 2H, J=6 Hz, CH$_2$O—), 1.82 (m, 2H, CH$_2$CH$_2$O—), 1.27 (m, 14H, CH$_2$) and 0.83 ppm (m, 3H, CH$_3$); fluorine nmr $\phi$75.4 (s); ir (CCl$_4$) 1420, 1220, 1160 and 950 cm$^{-1}$ (SO$_3$CF$_3$).

Anal. Calcd for C$_{11}$H$_{21}$F$_3$SO$_3$: C, 45.50; H, 7.29; S, 11.05. Found: C, 45.44; H, 7.09; S, 11.40.

Examples I and V typlify the effect that the solvent has on isomerization of the product in the type of reaction of the present invention. Examples II, III and VI to VIII demonstrate that the present process is able to produce organic perchlorates and triflates without appreciable isomerization for any organic group. Example IV further demonstrates the amount of isomerization which results from the use of the most commonly used solvent for this type of reaction. The inactivity, as noted in the examples between the aliphatic perchlorates or triflates with the corresponding silver salts, proves that the isomerization occurs before rather than after the product is formed. Thus the commonly used solvents must therefore effect the reaction mechanism.

Obviously many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A method of preparing alkyl perchlorate and triflates which comprises reacting at a temperature from about 5° C. to about 50° C. an alkyl iodide with a silver salt selected from the class consisting of silver perchlorate and silver triflate in an amount of benzene sufficient to provide at most a 75 percent product solution.

2. The method of claim 1 wherein said alkyl iodide is a primary alkyl iodide having from 3 to 10 carbon atoms.

3. The method of claim 2 wherein said reaction temperature is from 20° C. to 30° C.

4. The method of claim 3 wherein said alkyl iodide and said silver salt are reacted in a 1:1 salt-to-iodide mole ratio.

5. The method of claim 3 wherein said alkyl iodide and said silver salt are reacted in a salt-to-iodide mole ratio from 1.1:1 to 1.15:1.

6. The method of claim 4 wherein said benzene is present in an amount sufficient to provide a 20 percent product solution.

7. The method of claim 6 wherein said alkyl iodide is a primary alkyl iodide having from 3 to 6 carbon atoms.

8. The method of claim 7 wherein said alkyl iodide is a primary straight-chain alkyl iodide having from 3 to 6 carbon atoms.

9. The method of claim 1 wherein said silver salt is silver triflate.

10. The method of claim 9 wherein said alkyl iodide is propyl iodide.

* * * * *